United States Patent [19]
Dietz et al.

[11] Patent Number: 5,344,423
[45] Date of Patent: Sep. 6, 1994

[54] APPARATUS AND METHOD FOR MILLING BONE

[75] Inventors: Terry L. Dietz, Columbia City; Richard D. Vanlaningham, Leesburg, both of Ind.

[73] Assignee: Zimmer, Inc., Warsaw, Ind.

[21] Appl. No.: 832,098

[22] Filed: Feb. 6, 1992

[51] Int. Cl.⁵ .............................................. A61F 5/04
[52] U.S. Cl. ................................... 606/87; 606/86
[58] Field of Search ................ 606/88, 89, 86, 87, 606/96, 53, 100; 623/20, 16

[56] References Cited

U.S. PATENT DOCUMENTS

| | | | |
|---|---|---|---|
| 4,467,801 | 8/1984 | Whiteside | 182/303 R |
| 4,474,177 | 10/1984 | Whiteside | 128/303 R |
| 4,721,104 | 1/1988 | Kaufman et al. | 128/92 VW |
| 5,035,699 | 7/1991 | Coates | 606/86 |
| 5,047,032 | 9/1991 | Jellicoe | 606/83 |
| 5,098,436 | 3/1992 | Ferrante et al. | 606/88 |
| 5,100,409 | 3/1992 | Coates et al. | 606/87 |

FOREIGN PATENT DOCUMENTS

| | | | |
|---|---|---|---|
| 0337901A1 | 10/1989 | European Pat. Off. | A61B 17/14 |
| 415837 | 8/1990 | France | 606/87 |
| WO88/04912 | 7/1988 | PCT Int'l Appl. | A61B 17/14 |

Primary Examiner—Robert A. Hafer
Assistant Examiner—David J. Kenealy
Attorney, Agent, or Firm—Cary R. Reeves

[57] ABSTRACT

An apparatus and associated method are provided for milling bone. The apparatus includes a template having a reference surface for controlling depth of cut and a track for guiding the cutter in two dimensions to cut a planar surface.

5 Claims, 2 Drawing Sheets

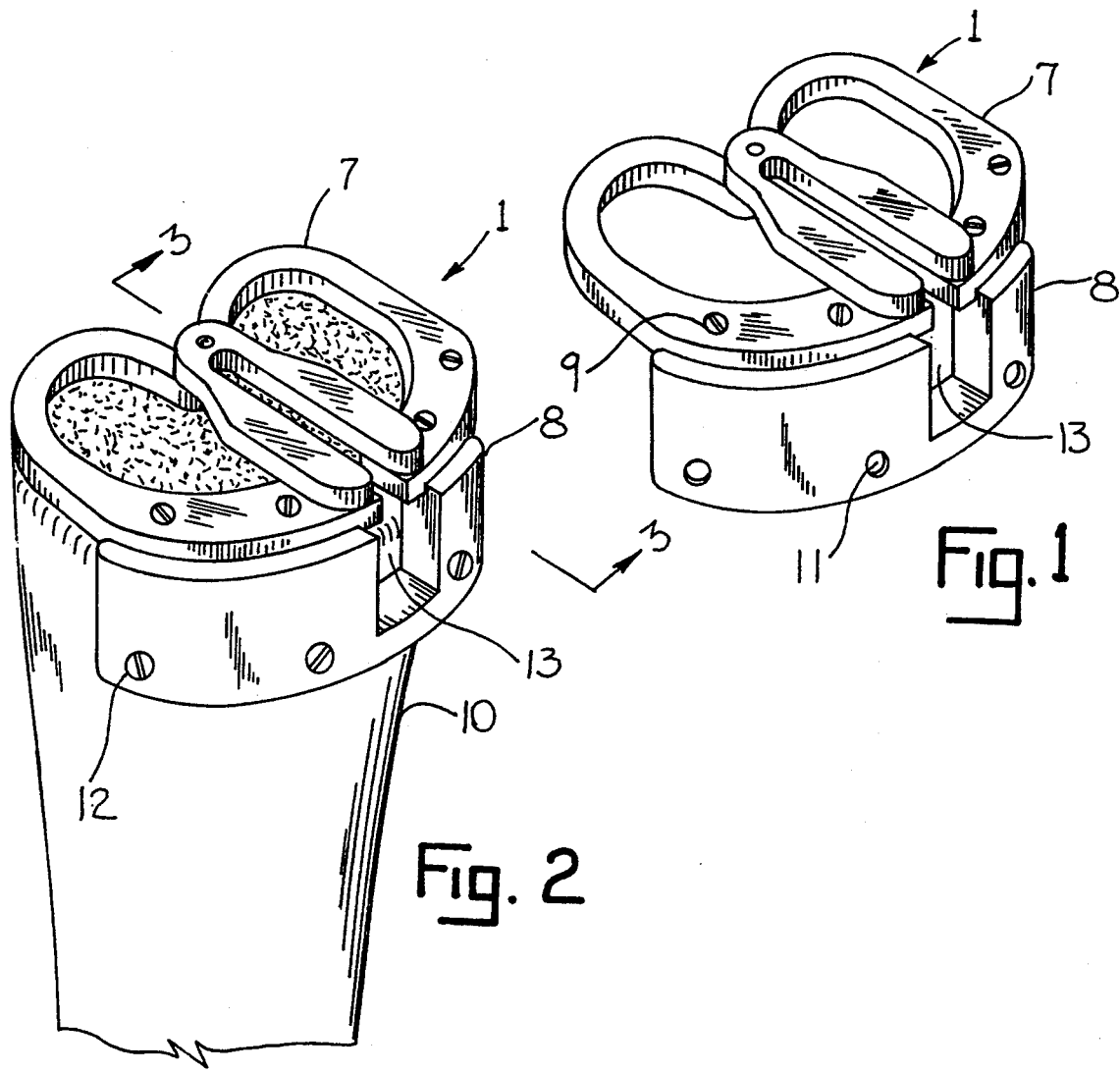
Fig. 1
Fig. 2
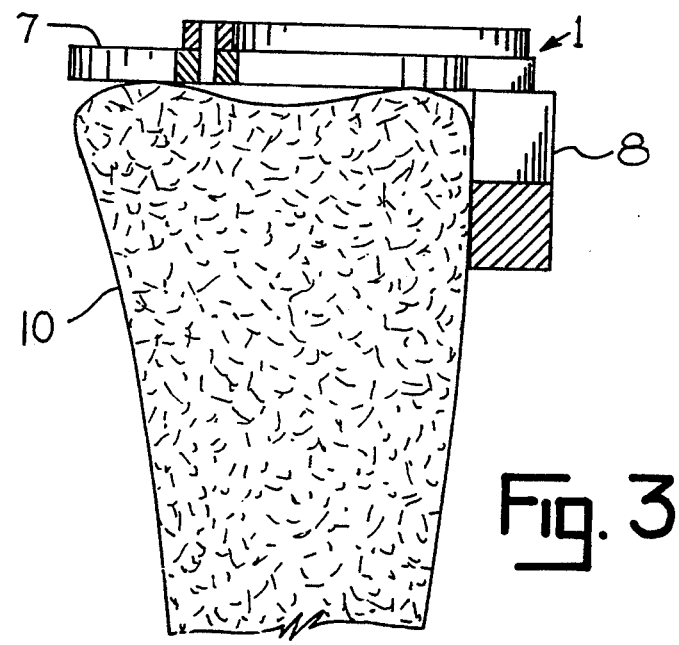
Fig. 3

APPARATUS AND METHOD FOR MILLING BONE

FIELD OF THE INVENTION

This invention relates to an apparatus and method for cutting bone and has specific relevance to an apparatus and method for milling a planar surface on a portion of a bone.

BACKGROUND OF THE INVENTION

Surgical procedures for removing a defective joint and replacing it with a prosthetic joint are well known. To accommodate the prosthetic joint it is very often necessary to remove a portion of the bone.

Heretofore, a generally flat surgical saw blade was used to cut the bone to remove the required portion of the bone. The saw blade could be either hand operated or powered in a reciprocating or oscillating motion. Typically, a guide would be connected adjacent the bone to guide the blade along the bone to assist in making a more precise cut. Typical saw blades are elongated and may bend slightly during cutting which can add to the inaccuracy of the cut or form small variations in the resulting surface requiring additional surface preparation before the prosthesis is attached.

SUMMARY OF THE INVENTION

The milling apparatus of this invention includes a guide connected to the exposed end portion of the bone by a plurality of screws or other fastening device. The guide includes a template having a reference surface which determines the milling depth. The guide also includes a track defined by the template to accommodate the shaft of a milling device. In use, a milling device is positioned such that the cutting teeth of the milling device are engageable with the bone stock to be removed. A shaft of the milling device extends through the track and is connectable to a rotary power source. While the power source drives it, the milling device is manually moved within the template as guided by the track of the template to mill the bone to a flat planar surface. Once the bone is milled, the guide is removed.

Accordingly, it is an object of the invention to provide a milling guide for a bone.

Another object of the invention is to provide a method of milling a bone.

Another object of the invention is to provide a bone milling guide having a track to accommodate a mill cutter.

Another object of the invention is to provide a bone milling guide wherein the track pivots within a fixed template.

Further objects of the invention will become apparent upon a reading of the following description taken with the accompanying drawings.

BRIEF DESCRIPTION OF THE DRAWINGS

FIG. 1 is a perspective view of the invention.

FIG. 2 is a perspective view of the invention connected to a tibia to be milled.

FIG. 3 is a sectional view taken along line 3—3 of FIG. 2.

DESCRIPTION OF THE PREFERRED EMBODIMENTS

Figure 4:
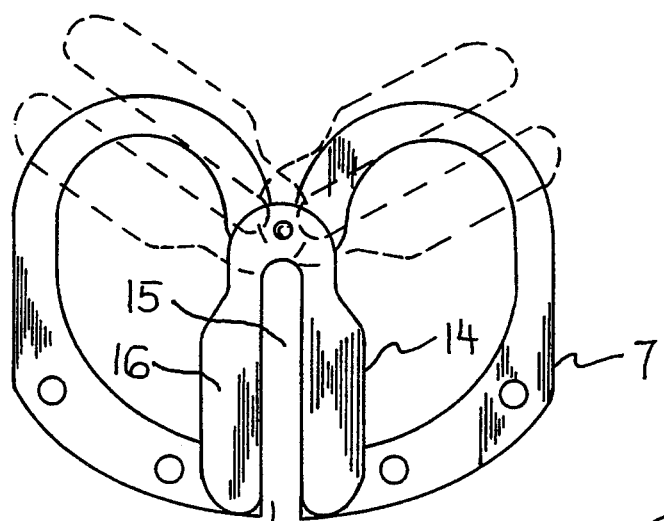
FIG. 4 is a plan view of the guide of FIGS. 1-3.

The preferred embodiments herein described are not intended to be exhaustive or to limit the invention to the precise forms disclosed. Rather, they are chosen and described to best explain the invention so that others skilled in the art might utilize their teachings.

Referring now to FIGS. 1-5 an exemplary apparatus for producing a planar surface on a portion of a tibia is illustrated and includes a guide 1 and a bone milling device. The bone milling device of FIG. 5 includes a burr 2 with a cutting portion 3 for milling bone and a shaft portion 4 connecting the cutting portion to a driving means. Preferably the cutting portion has cutting teeth on its distal end as well as along its sides. It may take the form of industrial end mills, router bits, or other suitable shape. While the shaft may engage the guide directly, it is preferable for the milling device to provide a guide engaging portion or nose 5 with a nose surface and an extending cannulated nipple 6. The shaft 4 extends through the nipple 6. The guide includes a template 7 and a base 8. The template is connected to the base by a plurality of screws 9 or some other fastening means. Even more preferably the template and base are integrated into a single piece. The base is slightly arcuate to conform to the outer contour of a patient's tibia 10 just below the knee joint. Transverse through bores 11 are formed in the base for accommodating bone screws 12 to connect the milling guide to the tibia. The base and template further have burr openings 13 and 20 to allow the burr to pass. The template is generally planar and includes a peripheral rim shaped as illustrated in the figures. In the embodiment of FIGS. 1-5, the template defines an open interior defining the limits of travel of the burr. It further comprises a pivot arm 14 which contains a slot or track 15 to accommodate the nipple 6 of the milling device. The top of the pivot arm forms a reference surface 16 engageable with the nose surface of the milling device, to control depth of cut.

In use, the guide is positioned at the desired height above the tibial articular surface by any method know in the art and securely fastened with bone screws through the base. The burr 2, connected to the power source, is placed in the burr openings 13 and 20 and the nose and nipple are placed adjacent the reference surface and track. With the burr being driven to cut bone, the pivot arm 14 is pivoted and the nipple 6 is moved along the track 15 to guide the burr so that it moves in two dimensions over the tibia to create a planar surface substantially parallel to the reference surface. After the tibia has been milled the guide is removed and a tibial plate prosthesis may be implanted.

Figure 6:
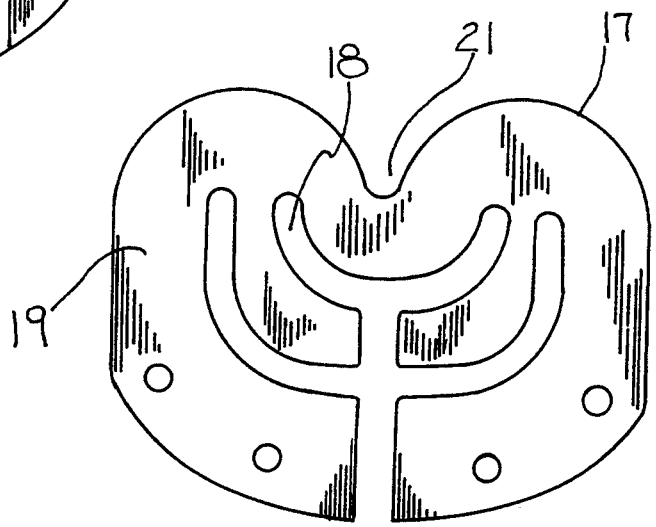
FIG. 6 is a plan view of a preferred embodiment of the guide of the invention.
Figure 5:
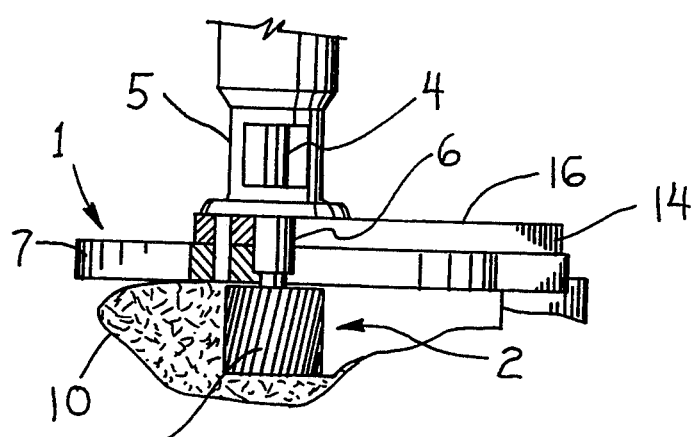
FIG. 5 is a sectional view of the proximal tibia being milled with a mill guided by the guide of the invention.

Another, more preferred, template embodiment is depicted in FIG. 6. The substantially planar template 17 contains a fixed track 18 for guiding the burr and a reference surface 19 to control depth of cut. The track is shaped so that a portion of the path that the burr cuts overlaps other portions of the path to yield a continuous planar cut surface. Burrs having different diameters might require different track shapes to achieve this result.

While the burr may be guided to cut an area that is within the periphery of the template or an area that extends beyond the template, it is preferable that the periphery of the template correspond to the outer limits of the path cut by the burr to allow an operator to determine precisely which tissues will be cut. It is also preferable to provide a variety of guides to accommodate a variety of bone sizes and shapes and variously shaped cut areas. For example, the exemplary guide shown provides an uncut posterior region 21 as would be suitable for a posterior cruciate ligament retaining tibial prosthesis.

While the preceding exemplary embodiments have focused on milling the tibial articular surface for a total knee joint prosthesis, it will be understood that the techniques described are applicable to unicondylar knee replacements as well as other joints and other bone surfaces, the guide geometry being adjusted accordingly. Likewise, it will be understood by those skilled in the art that numerous modifications to and departures from the embodiments hereinabove can be made without departing from the spirit and scope of the invention defined by the appended claims.

We claim:

1. An apparatus for producing a planar surface on a portion of a bone using a milling device, the apparatus comprising a template having a planar reference surface and defining a track means for guiding a said milling device in two dimensions, the reference surface and the track means engage said milling device, the track means guides a said milling device in two dimensions to form the planar surface on the bone parallel to the reference surface, the template defines an open interior and the reference surface comprises a pivot arm pivotably attached to the template.

2. An apparatus for producing a planar surface on a portion of a bone in order to prepare the bone to receive an implant comprising:
   a guide for mounting adjacent the bone, the guide having a planar reference surface and defining a track means for guiding a bone milling device in two dimensions; and
   a bone milling device having a cutting portion and a guide engaging portion; the guide engaging portion engaging the reference surface and the track means, the track means guiding the milling device in two dimensions to cut the bone a predetermined distance from the reference surface to produce the planar surface on the bone substantially parallel to the reference surface, the guide comprising a template defining an open interior, the reference surface comprising a pivot arm pivotably attached to the template.

3. A method of producing a planar surface on a portion of a bone using a bone milling device in order to prepare the bone to receive an implant comprising the steps of:
   mounting a template adjacent the bone to be prepared, the template having a planar reference surface and track means for guiding the milling device in two dimensions;
   positioning the bone milling device adjacent the template with a cutting portion directed against the bone and a first engaging means for engaging the template in contact with the reference surface and a second engaging means for engaging the template engaging the track means;
   driving the bone milling device to cut the bone;
   guiding the bone milling device over the bone;
   maintaining the first engaging means against the reference surface and the second engaging means in the track; and
   moving the cutting portion in two dimensions to cut the bone a predetermined distance from the reference surface to produce the planar surface substantially parallel to the reference surface.

4. A method of producing a planar surface on a portion of a bone using a bone milling device in order to prepare the bone to receive an implant comprising the steps of:
   mounting a template adjacent the bone to be prepared, the template having a planar reference surface comprising a pivot arm pivotably attached to the template and track means for guiding the milling device in two dimensions;
   positioning the bone milling device adjacent the template with a cutting portion directed against the bone and a first engaging means for engaging the template in contact with the reference surface and a second engaging means for engaging the template engaging the track means;
   driving the bone milling device to cut the bone;
   guiding the bone milling device over the bone;
   maintaining the first engaging means against the reference surface and the second engaging means in the track; and
   moving the cutting portion in two dimensions to cut the bone a predetermined distance from the reference surface to produce the planar surface substantially parallel to the reference surface.

5. The method of claim 3 wherein the template is of single piece construction and the track is formed in the template.

* * * * *